United States Patent [19]

Jensen-Korte et al.

[11] Patent Number: 4,803,215
[45] Date of Patent: Feb. 7, 1989

[54] 5-HETEROCYCLYL-1-ARYL-PYRAZOLES, COMPOSITION CONTAINING THEM, AND METHOD OF USING THEM TO COMBAT INSECTS, ACARIDS AND NEMATODES

[75] Inventors: Uta Jensen-Korte, Duesseldorf; Reinhold Gehring, Wuppertal; Otto Schallner, Monheim; Jörg Stetter, Wuppertal; Heinz-Jürgen Wroblowsky, Langenfeld; Benedikt Becker, Mettmann; Bernhard Homeyer, Leverkusen; Wolfgang Behrenz, Overath; Wilhelm Stendel, Wuppertal, all of Fed. Rep. of Germany

[73] Assignee: Bayer Aktiengesellschaft, Leverkusen, Fed. Rep. of Germany

[21] Appl. No.: 942,476

[22] Filed: Dec. 16, 1986

[30] Foreign Application Priority Data

Dec. 19, 1985 [DE] Fed. Rep. of Germany ....... 3545036

[51] Int. Cl.$^4$ .................. A02N 43/56; A02N 43/653; C07D 403/04
[52] U.S. Cl. .................................... 514/407; 514/383; 548/262; 548/362; 548/374
[58] Field of Search ...................... 548/262, 362, 374; 514/407, 383

[56] References Cited

U.S. PATENT DOCUMENTS 3,534,058 10/1970 Santilli et al. ...................... 548/375

FOREIGN PATENT DOCUMENTS 0201852 11/1986 European Pat. Off. ............ 548/374

Primary Examiner—Mary C. Lee
Assistant Examiner—Kurt G. Briscoe
Attorney, Agent, or Firm—Sprung Horn Kramer & Woods

[57] ABSTRACT

Pesticidally active 5-heterocyclyl-1-aryl-pyrazoles of the formula in which
$R^1$ represents hydrogen, alkyl or haloalkyl,
$R^2$ represents alkyl, alkenyl, alkinyl, cycloalkyl, haloalkyl, haloalkenyl, optionally substituted aralkyl or optionally substituted aryl,
Ar represents in each case optionally substituted phenyl or pyridyl,
Het represents a heterocycle of the formula n represents a number 0, 1 or 2,
where
$R^3$ and $R^4$, independently of one another, represent in each case hydrogen, alkyl or phenyl.
Intermediates of the formulas are provided, the former also being pesticidal.

18 Claims, No Drawings

5-HETEROCYCLYL-1-ARYL-PYRAZOLES, COMPOSITION CONTAINING THEM, AND METHOD OF USING THEM TO COMBAT INSECTS, ACARIDS AND NEMATODES

The invention relates to new 5-heterocyclyl-1-aryl-pyrazoles, several processes for their preparation and their use as pesticides.

It is already known that pyrazole derivatives, such as, for example, 1-cyclohexyl-5-[N,N-(dimethyl)-carbamoyloxy]-3-methylthiomethyl-pyrazole or 1-cyclohexyl-5-[N,N-(dimethyl)-carbamoyloxy]-3-methylsulphonylmethyl-pyrazole, have insecticidal properties (cf., for example, DE-OS (German Published Specification) No. 2,839,270).

The effectiveness or duration of action of these compounds is, however, not always completely satisfactory, particularly for certain insects or at low application concentrations.

New 5-heterocyclyl-1-aryl-pyrazoles of the general formula (I),

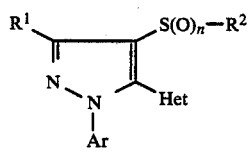

in which
$R^1$ represents hydrogen, alkyl or haloalkyl,
$R^2$ represents alkyl, alkenyl, alkinyl, cycloalkyl, haloalkyl, haloalkenyl, optionally substituted aralkyl or optionally substituted aryl,
Ar represents in each case optionally substituted phenyl or pyridyl,
Het represents a heterocycle of the formula

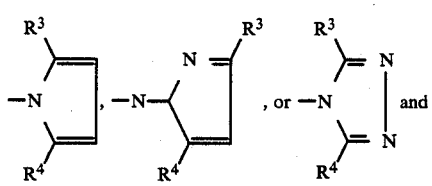

n represents a number 0, 1 or 2,
where $R^3$ and $R^4$, independently of one another, represent in each case hydrogen, alkyl or phenyl, have been found.

Furthermore, it has been found that the new 5-heterocyclyl-1-aryl-pyrazoles of the general formula (I)

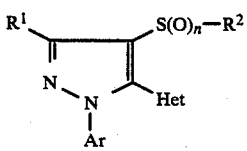

in which
$R^1$ represents hydrogen, alkyl or haloalkyl,
$R^2$ represents alkyl, alkenyl, alkinyl, cycloalkyl, haloalkyl, haloalkenyl, optionally substituted aralkyl or optionally substituted aryl,
Ar represents in each case optionally substituted phenyl or pyridyl,
Het represents a heterocycle of the formula

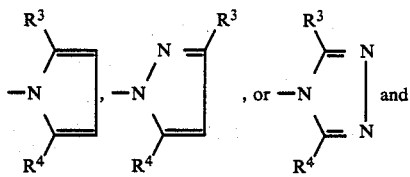

n represents a number 0, 1 or 2,
where $R^3$ and $R^4$, independently of one another, represent in each case hydrogen, alkyl or phenyl, are obtained by using one of the preparative processes described below:

(a) 5-Pyrrolyl-1-aryl-pyrazoles of the formula (Ia),

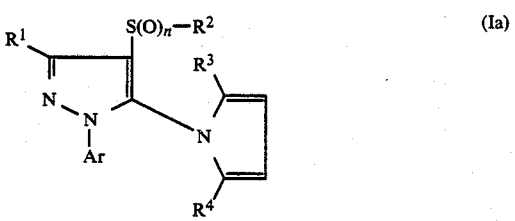

in which $R^1$, $R^2$, $R^3$, $R^4$, n and Ar have the abovementioned meaning, are obtained when 5-amino-1-aryl-pyrazoles of the formula (II)

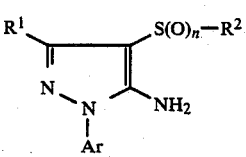

in which $R^1$, $R^2$, Ar and n have the abovementioned meaning, are reacted (α) with 1,4-dicarbonyl compounds of the formula (IIIa),

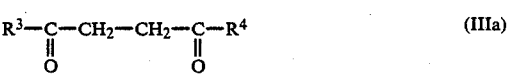

in which $R^3$ and $R^4$ have the abovementioned meaning, or (β) with their acetals or ketals of the formula (IIIb),

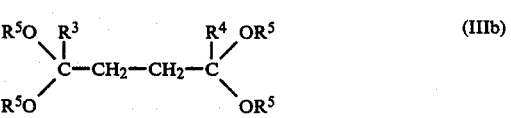

in which
$R^3$ and $R^4$ have the abovementioned meaning and
$R^5$ represents alkyl, or (γ) with their cyclic acetal structures of the formula (IIIc),

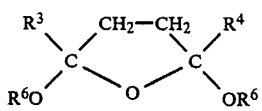 (IIIc)

in which

R³ and R⁴ have the abovementioned meaning and R⁶ represents alkyl, in each case if appropriate in the presence of a diluent and if appropriate in the presence of a reaction auxiliary;

(b) 5-(pyrazol-1-yl)-1-aryl-pyrazoles of the formula (Ib),

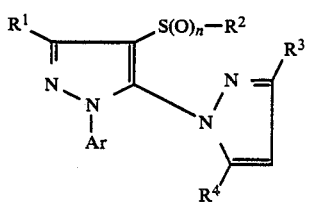 (Ib)

in which $R^1$, $R^2$, $R^3$, $R^4$, Ar and n have the abovementioned meaning, are obtained when 5-hydrazino-1-aryl-pyrazoles of the formula (IV),

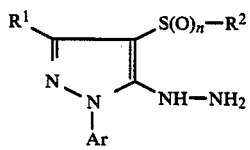 (IV)

in which $R^1$, $R^2$, Ar and n have the abovementioned meaning, are reacted (α) with 1,3-dicarbonyl compounds of the formula (Va),

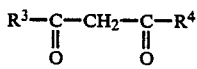 (Va)

in which $R^3$ and $R^4$ have the abovementioned meaning, or (β) with their acetals or ketals of the formula (Vb),

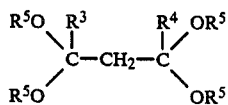 (Vb)

in which $R^3$, $R^4$ and $R^5$ have the abovementioned meaning, in each case if appropriate in the presence of a diluent and if appropriate in the presence of a reaction auxiliary;

(c) 5-(1,3,4-triazol-1-yl)-1-aryl-pyrazoles of the formula (Ic),

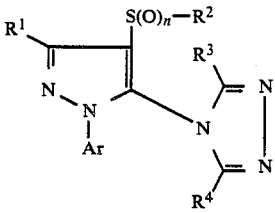 (Ic)

in which $R^1$, $R^2$, $R^3$, $R^4$, Ar and n have the above mentioned meaning, are obtained when 5-amino-1-aryl-pyrazoles of the formula (II),

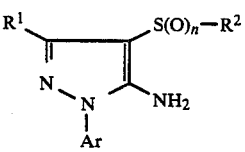 (II)

in which $R^1$, $R^2$, Ar and n have the abovementioned meaning, are reacted with diacyl-hydrazines of the formula (VI),

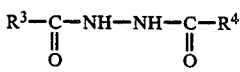 (VI)

in which $R^3$ and $R^4$ have the abovementioned meaning, if appropriate in the presence of a diluent.

Finally, it has been found that the new 5-heterocyclyl-1-aryl-pyrazoles of the general formula (I) have very pronounced pesticidal and, in particular, insecticidal properties.

Surprisingly, the 5-heterocyclyl-1-aryl-pyrazoles according to the invention of the general formula (I) have considerably better insecticidal effectiveness than the pyrazole derivatives known from the prior art, such as, for example, 1-cyclohexyl-5-[N,N-(dimethyl)-carbamoyloxy]-3-methylthiomethyl-pyrazole or 1-cyclohexyl-5-[N,N-(dimethyl)-carbamoyloxy]-3-methylsulphonyl-pyrazole, which are similar compounds chemically and regarding their action.

The 5-heterocyclyl-1-aryl-pyrazoles according to the invention are generally defined by the formula (I).

Those compounds of the formula (I) are preferred in which $R^1$ represents in each case straight-chain or branched alkyl or haloalkyl having 1 to 4 carbon atoms and, if appropriate, 1 to 9 identical or different haloatoms or represents hydrogen, $R^2$ represents in each case straight-chain or branched alkyl, alkenyl or alkinyl having in each case up to 8 carbon atoms, represents in each case straight-chain or branched haloalkyl or haloalkenyl having in each case up to 8 carbon atoms and up to 17 identical or different haloatoms, represents cycloalkyl having 3 to 7 carbon atoms or represents in each case optionally singly or multiply, identically or differently substituted phenylalkyl or phenyl having, if appropriate, 1 to 4 carbon atoms in the straight-chain or branched alkyl part, suitable phenyl substituents in each case being: halogen, cyano, nitro, in each case straight-chain or branched alkyl, alkoxy, alkylthio, alkylsulphinyl, alkylsulphonyl, haloalkyl, haloalkoxy, haloalkylthio, haloalkylsulphinyl or haloalkylsulphonyl having in each case 1 to 4 carbon atoms in the individual alkyl parts and, if appropriate, having 1 to 9 identical or different haloatoms, Ar represents in each case optionally singly or multiply, identically or differently substituted phenyl, 2-pyridyl, 3-pyridyl or 4-pyridyl, suitable substituents being: cyano, nitro, halogen, in each case straight-chain or branched alkyl, alkoxy or alkoxycarbonyl having in each case up to 4 carbon atoms, in addition in each case straight-chain or branched haloalkyl or haloalkoxy having in each case up to 4 carbon atoms and up to 9 identical or different haloatoms or an —S(O)$_m$—R$^7$ radical where R$^7$ represents amino, or in each case straight-chain or branched alkyl, alkylamino, dialkylamino or haloalkyl having in each case up to 4 carbon atoms in the individual alkyl parts and, in the case of the haloalkyl, having up to 9 identical or different haloatoms and m represents a number 0, 1 or 2, n also represents a number 0, 1 or 2 and Het represents a

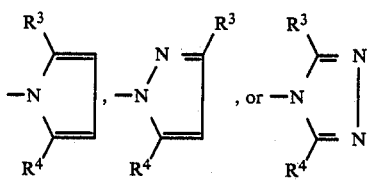

radical, where

R$^3$ and R$^4$, independently of one another, represent in each case hydrogen, straight-chain or branched alkyl having 1 to 4 carbon atoms, or phenyl. Those compounds of the formula (I) are particularly preferred in which R$^1$ represents hydrogen, methyl, ethyl, n- or i-propyl or trifluoromethyl, R$^2$ represents methyl, ethyl, n- or i-propyl, n-, i-, s- or t-butyl, n- or i-pentyl, n- or i-hexyl, allyl, propenyl, butenyl, propargyl, butinyl, cyclopropyl, cyclopentyl, cyclohexyl, chloromethyl, difluoromethyl, difluorochloromethyl, fluorodichloromethyl, trifluoromethyl, pentafluoroethyl, pentachloroethyl, fluorotetrachloroethyl, difluorotetrachloroethyl, trifluorodichloroethyl, tetrafluorochloroethyl, heptafluoropropyl, chloroethyl, bromoethyl, chloropropyl, chloropropenyl, dichloropropenyl, chlorobutenyl, or in each case optionally singly to triply, identically or differently substituted phenyl, benzyl or phenylethyl, suitable phenyl substituents being: fluorine, chlorine, bromine, iodine, cyano, nitro, methyl, ethyl, methoxy, methylthio, trifluoromethyl, methylsulphinyl, methylsulphonyl, trifluoromethoxy, trifluoromethylthio, trifluoromethylsulphinyl or trifluoromethylsulphonyl, Ar represents in each case optionally singly to quintuply, identically or differently substituted phenyl, 2-pyridyl, 3-pyridyl or 4-pyridyl, suitable substituents being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluormethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an —S(O)$_m$—R$^7$ radical where R$^7$ represents amino, methylamino, ethylamino, dimethylamino, diethylamino, fluorodichloromethyl, difluoromethyl, tetrafluoroethyl, trifluorochloroethyl, trifluoromethyl, methyl or ethyl, m represents a number 0, 1 or 2, n also represents a number 0, 1 or 2 and Het represents a heterocycle of the formula

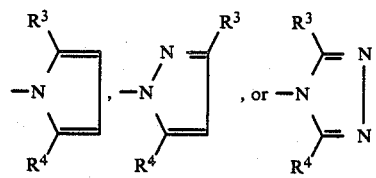

where R$^3$ and R$^4$, independently of one another, in each case represent hydrogen, methyl, ethyl, n- or i-propyl or phenyl.

In detail, apart from the compounds mentioned in the preparation examples, the following 5-heterocyclyl-1-aryl-pyrazoles of the general formula (I)

$$\text{(I)}$$

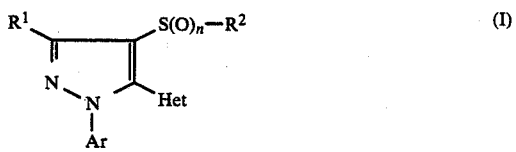

may be mentioned:

| R$^1$ | —S(O)$_n$—R$^2$ | Het | Ar |
|---|---|---|---|
| H | SCF$_3$ | -N⟨pyrazole⟩ | 2,6-Cl$_2$-4-CF$_3$-phenyl |
| H | SCCl$_2$F | -N⟨pyrazole⟩ | 2,6-Cl$_2$-4-CF$_3$-phenyl |
| H | SCClF$_2$ | -N⟨pyrazole⟩ | 2,6-Cl$_2$-4-CF$_3$-phenyl |

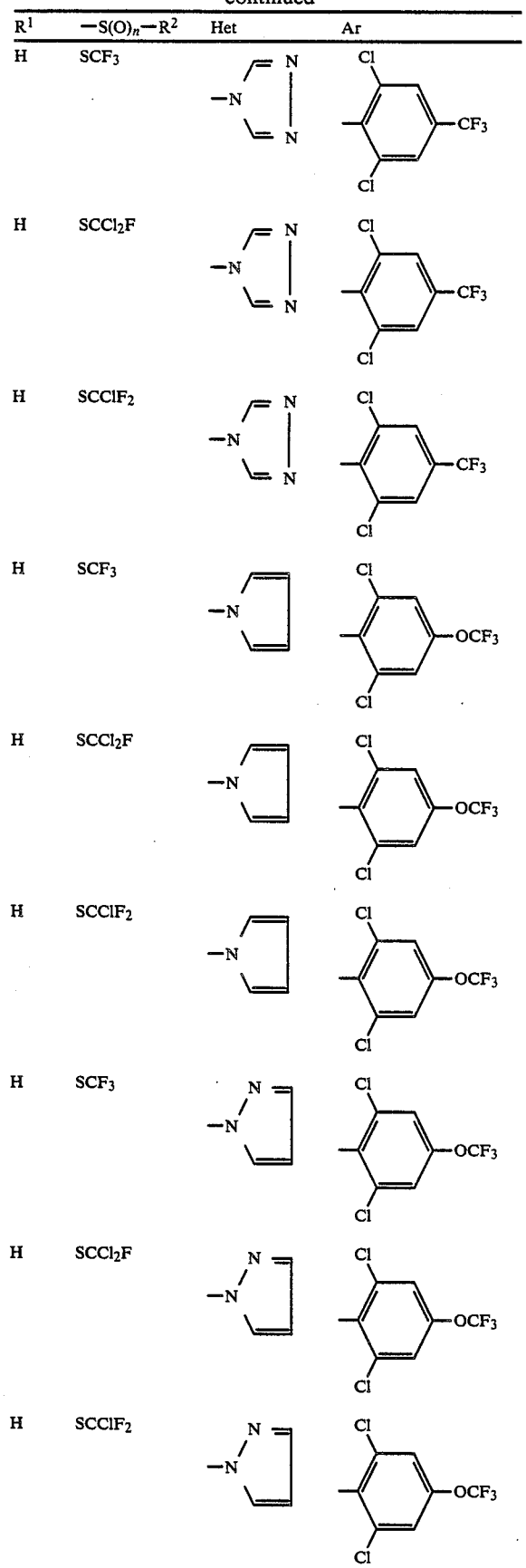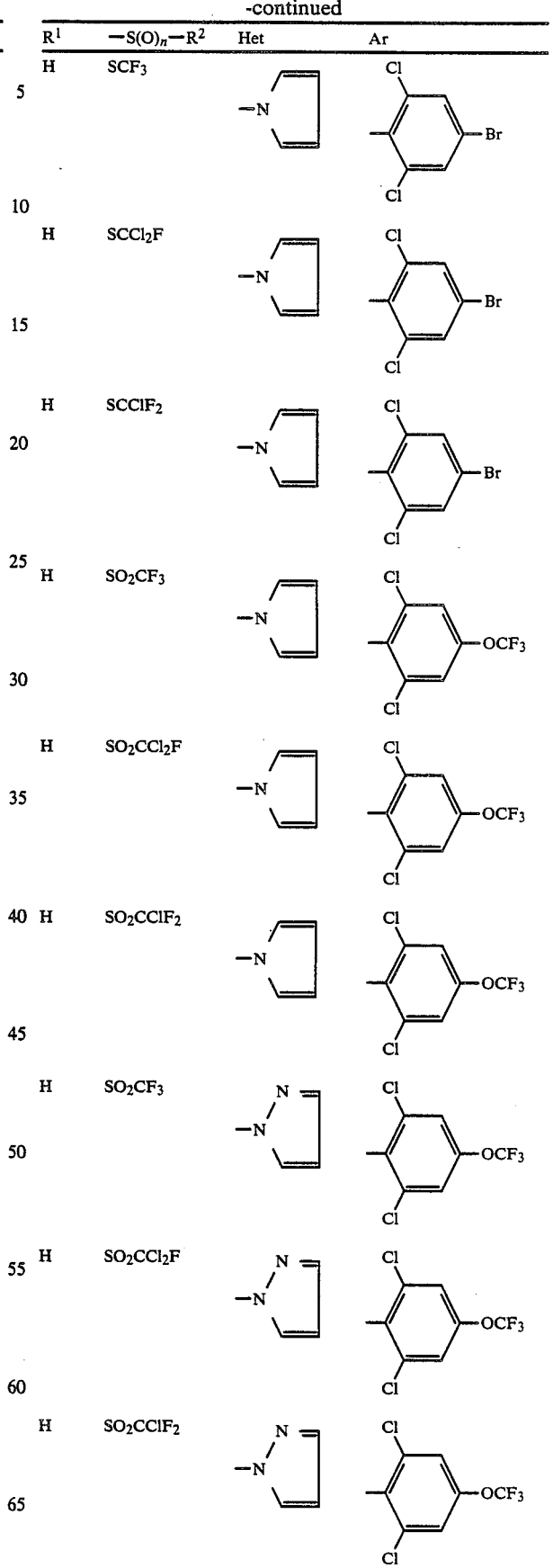

-continued

| $R^1$ | $-S(O)_n-R^2$ | Het | Ar |
|---|---|---|---|
| CH$_3$ | SCF$_3$ | | |
| CH$_3$ | SCCl$_2$F | | |
| CH$_3$ | SCClF$_2$ | | |
| CH$_3$ | SCF$_3$ | | |
| CH$_3$ | SCCl$_2$F | | |
| CH$_3$ | SCClF$_2$ | | |
| CH$_3$ | SO$_2$CF$_3$ | | |
| CH$_3$ | SO$_2$CCl$_2$F | | |

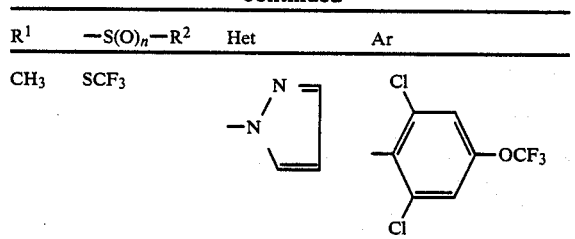
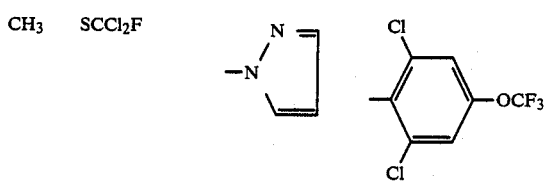
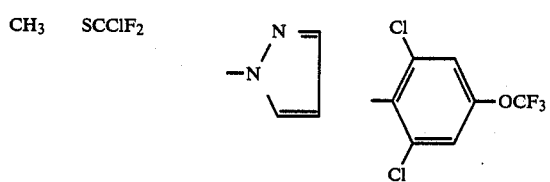
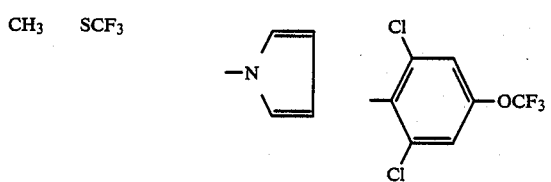
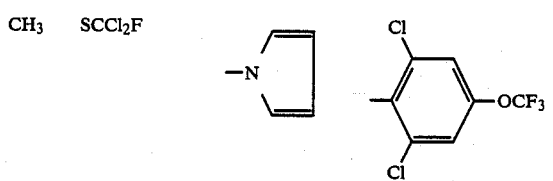
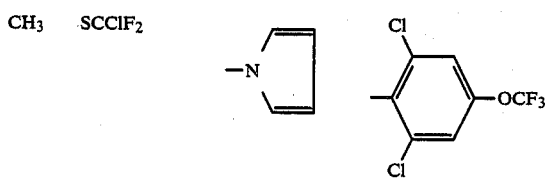
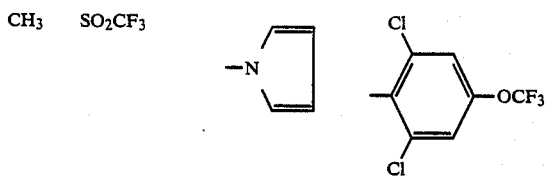
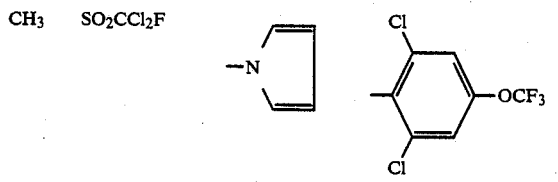

-continued

| $R^1$ | $-S(O)_n-R^2$ | Het | Ar |
|---|---|---|---|
| CH$_3$ | SO$_2$CClF$_2$ | | |

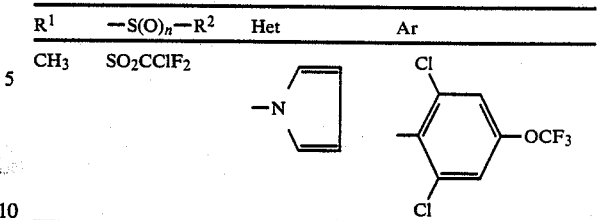

If, for example, 5-amino-1-phenyl-4-dichlorofluoromethylsulphenyl-pyrazole and 2,5-diethoxytetrahydrofuran are used as starting materials, then the course of the reaction of the process (a) according to the invention can be represented by the following scheme:

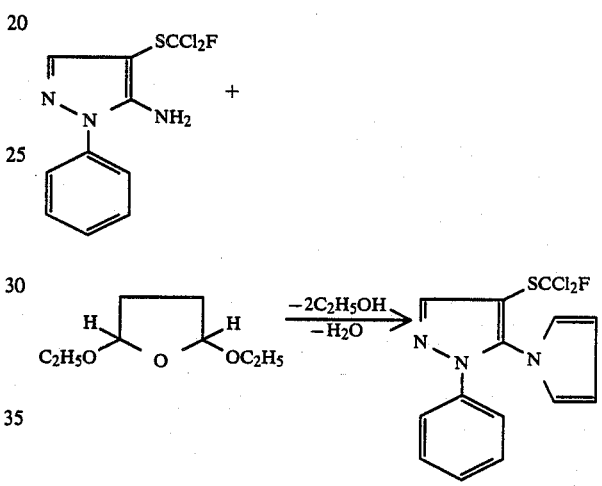

If, for example, 1-(2,6-dichloro-4-trifluoromethylphenyl)-5-hydrazino-4-trifluoromethylsulphonyl-pyrazole and 1,1,3,3-tetramethoxypropane are used as starting materials, then the course of the reaction of the process (b) according to the invention can be represented by the following scheme:

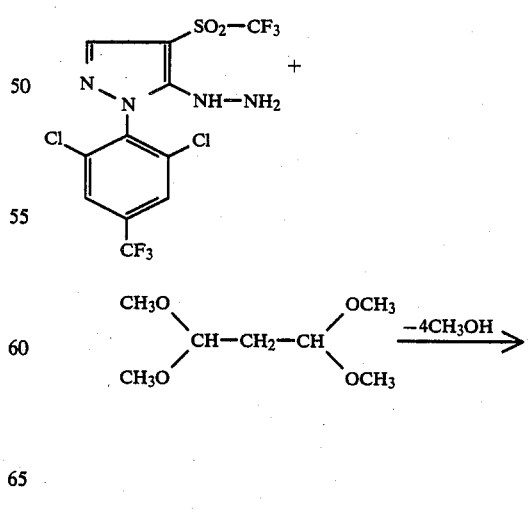

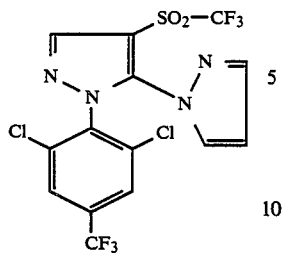

If, for example, 5-amino-4-methylthio-3-methyl-1-(2,4,6-trichlorophenyl)-pyrazole and 1,2-dibenzoylhydrazine are used as starting materials, then the course of the reaction of the process (c) according to the invention can be represented by the following scheme:

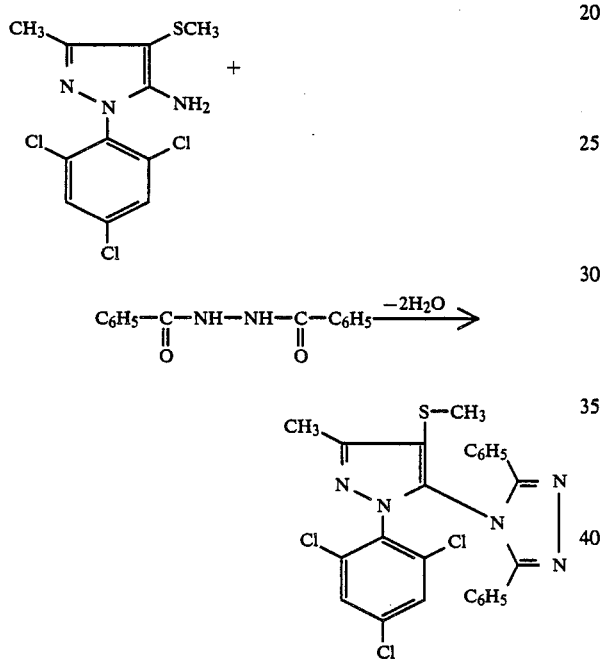

The 5-amino-1-aryl-pyrazoles which are necessary as starting materials to carry out the processes (a) and (c) according to the invention are generally defined by the formula (II). In this formula (II), $R^1$, $R^2$, Ar and n preferably represent those radicals which have already been mentioned as being preferred for these substituents in connection with the description of the substances of the formula (I) according to the invention.

Some 5-amino-1-aryl-pyrazoles of the formula (II) are known (cf., for example, Pharmaco. Ed. Sci. 26, 276-293 [1971] or Mycopathologica 74, 7-14 [1981] also cf. C.A. 96: 196411j or C.A. 95: 36257q; DE-OS (German Published Specification) No. 3,402,308); some of them are the subject of commonly assigned patent application Ser. No. 858,475, filed Apr. 30, 1986, now pending, corresponding to DE-P (German Patent Application) No. 3,517,843) and can be obtained in analogous fashion to the preparative processes described therein, for example if 4-thiocyanato-5-aminopyrazoles of the general formula (VII),

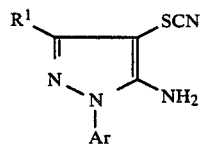

in which $R^1$ and Ar have the abovementioned meaning, or bis-(pyrazolyl) disulphides of the formula (VIII),

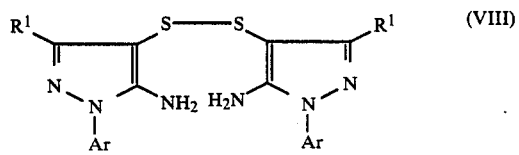

in which $R^1$ and Ar have the abovementioned meaning, are reacted with halides of the formula (IX),

in which
$R^2$ has the abovementioned meaning and
Hal represents halogen, particularly chlorine or bromine,
if appropriate in the presence of a diluent, such as, for example, methanol, and in the presence of a suitable reducing agent, such as, for example, sodium borohydride or sodium dithionite, and in the presence of a base, such as, for example, potassium hydroxide, at temperatures between 20° C. and 90° C., or if 4-unsubstituted 5-amino-pyrazoles of the formula (X),

in which
$R^1$ and Ar have the abovementioned meanings, are reacted with sulphenyl halides of the formula (XI)

in which
$R^2$ has the abovementioned meaning and
Hal' represents halogen, particularly chlorine or bromine,
if appropriate in the presence of a diluent, such as, for example, dichloromethane, and if appropriate in the presence of an acid binder, such as, for example, pyridine, at temperatures between 0° C. and 50° C.; or if the 5-aminopyrazoles, obtainable according to the process described above, of the formula (IIa),

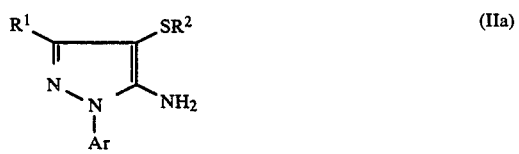

in which $R^1$, $R^2$ and Ar have the abovementioned meaning, are oxidized at the sulphur of the sulphenyl group in the 4-position of the pyrazole ring using oxidants of the formula (XII),

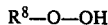 (XII)

in which $R^8$ represents hydrogen or in each case optionally substituted alkanoyl or aroyl, particularly hydrogen, acetyl, propionyl, trifluoroacetyl or optionally substituted benzoyl, such as, for example, 3-chlorobenzoyl or 4-nitrobenzoyl, if appropriate in the presence of a diluent, such as, for example, dichloromethane, if appropriate in the presence of a catalyst, such as, for example, ammonium molybdate, and if appropriate in the presence of an acid binder, such as, for example, sodium carbonate, at temperatures between 0° C. and +50° C.

Some 4-thiocyanato-5-aminopyrazoles of the formula (VII) are known (cf., for example, Pharmaco Ed. Sci. 38, 274–282 [1983]). They are obtained, for example, when 4-unsubstituted 5-aminopyrazoles of the formula (X),

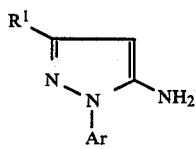 (X)

in which $R^1$ and Ar have the abovementioned meaning, are reacted with ammonium thiocyanate in the presence of bromine and acetic acid at temperatures between −20° C. and +20° C.

The bis-(pyrazolyl) disulphides of the formula (VIII) are not yet known. They are obtained when the 4-thiocyanato-5-amino-pyrazoles of the formula (VII) described above are reacted with aqueous hydrochloric acid, if appropriate in the presence of a diluent, such as, for example, ethanol, at temperatures between 20° C. and 120° C.

The 4-unsubstituted 5-aminopyrazoles of the formula (X) are known (cf., for example, J. Org. Chem. 36, 2972–2974 [1971] or J. Heterocyclic Chemistry 7, 345–349 [1970]; C.A. 62: 13137c or DE-OS (German Published Specification) No. 3,402,308) or can be obtained in a simple analogous fashion according to known processes (cf. also the preparation examples).

The halides of the formula (IX), the sulphenyl halides of the formula (XI) and the oxidants of the formula (XII) are generally known compounds of organic chemistry.

The 1,4-dicarbonyl compounds, or their acetals, ketals or cyclic acetal structures, which are furthermore required as starting materials to carry out the process (a) according to the invention are generally defined by the formulae (IIIa–c). In these formulae (IIIa–c), $R^3$ and $R^4$ preferably represent those radicals which have already been mentioned in connection with the description of the substances of the formula (I) according to the invention as being preferred for these substituents.

In the formula (IIIb), $R^5$ preferably represents straight-chain or branched alkyl having 1 to 4 carbon atoms, particularly methyl or ethyl. In the formula (IIIc), $R^6$ preferably also represents straight-chain or branched alkyl having 1 to 4 carbon atoms, particularly methyl or ethyl.

The 1,4-dicarbonyl compounds of the formula (IIIa), their acetals or ketals of the formula (IIIb) and their cyclic acetal structures of the formula (IIIc) are generally known compounds of organic chemistry.

The 5-hydrazino-1-aryl-pyrazoles which are required as starting materials to carry out the process (b) according to the invention are generally defined by the formula (IV). In this formula (IV), $R^1$, $R^2$, Ar and n preferably represent those radicals which have already been mentioned in connection with the description of the substances of the formula (I) according to the invention as being preferred for these substituents.

The 5-hydrazino-1-aryl-pyrazoles of the formula (IV) are not yet known. The compounds of the formula (IV) also have a strong pesticidal and particularly insecticidal action.

They are obtained when 5-amino-1-aryl-pyrazoles of the formula (II),

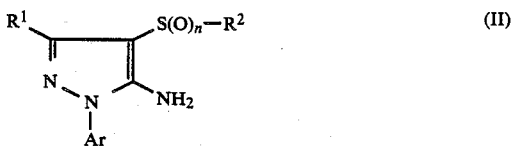 (II)

in which $R^1$, $R^2$, Ar and n have the abovementioned meaning, are initially, in a first stage, diazotized in a conventional manner using nitrite compounds of the formula (XIII),

 (XIII)

in which $R^9$ represents hydrogen, alkyl or an alkali metal cation, in the presence of a hydrohalic acid, such as, for example, hydrochloric acid or hydrobromic acid, or in the presence of a haloform, such as, for example, chloroform or bromoform, at temperatures between −20° C. and +80° C. (cf., for example, "Organikum" 15th edition VEB Deutscher Verlag der Wissenschaften, Berlin, 1981, page 652 et seq.; J. Chem. Soc. C. 1966, 1249 or Rev. Latinoam. Quim. 13, 100–102 [1982]), and the 5-halo-1-aryl-pyrazoles of the formula (XIV) thus obtained,

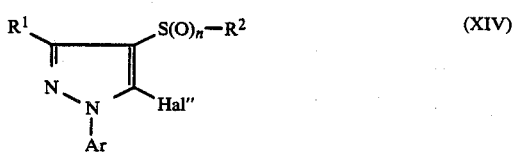 (XIV)

in which
$R^1$, $R^2$, Ar and n have the abovementioned meaning and Hal″ represents halogen, particularly chlorine or bromine,
are reacted with hydrazine hydrate, if appropriate in the presence of a diluent, such as, for example, dioxane, at temperatures between 20° C. and 120° C.

The nitrite compounds of the formula (XIII) are generally known compounds of organic chemistry.

The 1,3-dicarbonyl compounds or their acetals or ketals which are furthermore required as starting materials to carry out the process (b) according to the invention are generally defined by the formulae (Va) and (Vb). In these formulae (Va) and (Vb), $R^3$ and $R^4$ preferably represent those radicals which have already been mentioned in connection with the description of the substances of the formula (I) according to the invention as being preferred for these substituents.

$R^5$ in formula (Vb) preferably represents straight-chain or branched alkyl having 1 to 4 carbon atoms, particularly methyl or ethyl.

The 1,3-dicarbonyl compounds of the formula (Va) and their acetals or ketals of the formula (Vb) are generally known compounds of organic chemistry.

The diacyl hydrazines which are furthermore required as starting materials to carry out the process (c) according to the invention are generally defined by the formula (VI). In this formula (VI), $R^3$ and $R^4$ preferably represent those radicals which have already been mentioned in connection with the description of the substances of the formula (I) according to the invention as being preferred for these substituents.

The diacyl hydrazines of the formula (VI) are also generally known compounds of organic chemistry.

Suitable diluents for carrying out the process (a) according to the invention are inert organic solvents.

To this group belong in particular aliphatic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl or diethyl ether, alcohols, such as methanol, ethanol or propanol, mixtures of these with water or acids, such as acetic acid, or mixtures of these with water.

The process (a) according to the invention is, if appropriate, carried out in the presence of a suitable reaction auxiliary. As such, inorganic or organic acids, such as, for example, acetic acid or p-toluenesulphonic acid, are preferably used.

The reaction temperatures can be varied within a relatively wide range when the process (a) according to the invention is carried out. In general, the reaction is carried out at temperatures between 20° C. and 200° C., preferably at temperatures between 60° C. and 150° C.

To carry out the process (a) according to the invention, 1.0 to 10.0 moles, preferably 2.0 to 5.0 moles, of 1,4-dicarbonyl derivative of the formula (IIIa), (IIIb) or (IIIc) and, if appropriate, 0.001 to 10.0 moles, preferably 0.01 to 5.0 moles, of reaction auxiliary are, in general, employed per mole of 5-amino-1-aryl-pyrazole of the formula (II). The reaction is carried out, and the reaction products of the formula (Ia) are worked up and isolated according to generally conventional methods.

Suitable diluents for carrying out the process (b) according to the invention are also inert organic solvents. The solvents listed for process (a) are preferably used.

The process (b) according to the invention is, if appropriate, also carried out in the presence of a suitable reaction auxiliary. As such, the reaction auxiliaries listed for process (a) are preferably used.

The reaction temperatures can also be varied within a relatively wide range when the process (b) according to the invention is carried out. In general, the reaction is carried out at temperatures between 0° C. and 200° C., preferably at temperatures between 50° C. and 150° C.

To carry out the process (b) according to the invention, 1.0 to 10.0 moles, preferably 2.0 to 5.0 moles, of 1,3-dicarbonyl compound of the formula (Va) or (Vb) and, if appropriate, 0.001 to 10.0 moles, preferably 0.01 to 5.0 moles, of reaction auxiliary are, in general, employed per mole of 5-hydrazino-1-aryl-pyrazole of the formula (IV).

The reaction is carried out and the reaction products of the formula (Ib) are worked up and isolated according to generally conventional methods.

Suitable diluents for carrying out the process (c) according to the invention are also inert organic solvents. The solvents listed for process (a) are preferably used.

The process (c) according to the invention is, if appropriate, also carried out in the presence of a suitable reaction auxiliary. As such, the reaction auxiliaries listed for process (a) are preferably used.

The reaction temperatures can also be varied within a relatively wide range when the process (c) according to the invention is carried out. In general, the reaction is carried out at temperatures between 0° C. and 200° C., preferably at temperaures between 50° C. and 150° C.

To carry out the process (c) according to the invention, 1.0 to 10.0 moles, preferably 2.0 to 5.0 moles, of diacyl hydrazine of the formula (VI) and, if appropriate, 0.001 to 10.0 moles, preferably 0.01 to 5 moles, of reaction auxiliary are, in general, employed per mole of 5-amino-1-aryl-pyrazole of the formula (II).

The reaction is carried out and the reaction products of the formula (Ic) are worked up and isolated according to generally conventional methods.

The active compounds of the general formulae (I) and (IV) are suitable for combating animal pests, in particular insects, arachnida and nematodes, encountered in agriculture, in forestry, in the protection of stored products and of materials, and in the hygiene field, and have good plant tolerance and favorable toxicity to warm-blooded animals. They are active against normally sensitive and resistant species and against all or some stage of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermaptera, for example *Forficula auricularia*. From the order of the Isoptera, for example, Reticulitermes spp. From the order of the Anoplura, for example, *Phylloxera vastatrix*, Pemphigus spp., *Pediculus humanus corporis*, Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinus, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata* lugens, Aonidiella aurantii, Aspidiotus hederae, Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and Costelytra zealandica. From the order of the Hymenoptera, for example, Diprion spp., Hoplocampa spp., Lasium spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.*

The active compounds according to the invention are not only active against plant, hygiene and stored product pests, but also, in the veterinary medicine sector, against animal parasites (ectoparasites), such as scaly ticks, argasidae, scab mites, trombidae, flies (stinging and sucking), parasitic fly larvae, lice, hair lice, bird lice and fleas. They are active against normally sensitive and resistant species and strains, as well as against all parasitic and non-parasitic stages of development of the ectoparasites.

The active compounds according to the invention have a strong insecticidal action. They can be employed particularly successfully against insects which are harmful to plants, such as, for example, against the larvae of the horseradish leaf beetle (*Phaedon cochleariae*) and against the larvae of the cabbage moth (*Plutella maculipennis*).

In addition, they are also extremely suitable for combating soil insects and can be employed, for example, for combating Phorbia antiqua grubs.

In addition, the active compounds according to the invention have a high activity against hygiene pests and stored product pests and can be employed, for example, for combating cockroaches (*Blattella germanica*) the house fly (Musca domestica) or for combating the grain weevil (Sitophilus granarius). In addition, the active compounds according to the invention can be particularly successfully used for combating pests which live parasitically on warm-blooded animals, such as, for example, against the larvae of the sheep maggot fly (*Lucilia cuprina*). Besides this, the active compounds according to the invention have a good fungicidal action when applied in appropriate amounts and can be employed, for example, for combating Botrytis and Venturia species. The intermediates of the formula (IV) also have good insecticidal properties.

The active compounds can be converted to the customary formulations, such as solutions, emulsions, suspensions, powders, foams, pastes, granules, aerosols, natural and synthetic materials impregnated with active compound, very fine capsules in polymeric subtances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such s chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds which can be used according to the invention are also suitable for combating insects, midges, ticks etc. in the sectors of animal keeping and cattle breeding; better results, for example higher milk production, greater weight, more attractive animal pelt, longer life etc., can be achieved by combating the pests.

The application of the active compounds which can be used according to the invention occurs in this sector in a known fashion, such as by oral application in the form of, for example, tablets, capsules, potions, granules, by means of dermal or external application in the form of, for example, dipping, spraying, pouring-on, spotting-on and dusting, as well as by means of parenteral application in the form, for example, of injection, and, furthermore, by means of the feed-through process. In addition, application as molded articles (neckband, ear tag) is also possible.

The biological effectiveness of the compounds according to the invention will be explained with reference to the examples below.

PREPARATION EXAMPLES

Example 1

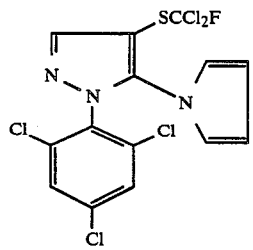

10 g (0.025 mole) of 5-amino-4-dichlorofluoromethylthio-1-(2,6-dichloro-4-trifluoromethyl-phenyl)-pyrazole and 8.8 g (0.055 mole) of 2,5-diethoxytetrahydrofuran are refluxed for 4 hours in 60 ml of glacial acetic acid. For work-up, the cooled reaction mixture is poured into water, extracted several times using dichloromethane and dried over sodium sulphate, and the solvent is removed in vacuo. The residue crystallizes on trituration with ligroin. 8.5 g (71% of theory) of 1-(2,6-dichloro-4-trifluoromethyl-phenyl)-5-(pyrrol-1-yl)-4-dichlorofluoromethylsulphenyl-pyrazole of melting point 93° C. are obtained.

PREPARATION OF THE STARTING COMPOUNDS

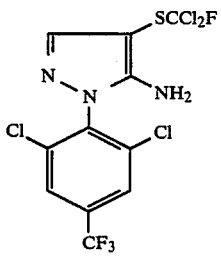

10 g (0.034 mole) of 5-amino-1-(2,6-dichloro-4-trifluoromethyl)-pyrazole are dissolved in 50 ml of glacial acetic acid and treated dropwise with 6.1 g (0.036 mole) of dichlorofluoromethanesulphenyl chloride at room temperature. The temperature rises to about 40° C. The reaction mixture is stirred for 2 hours and then poured into a mixture of 200 ml of water and 50 ml of dichloromethane. The organic phase is separated off, and the aqueous phase is extracted with twice 20 ml of dichloromethane. The combined organic phases are washed in sequence with sodium hydrogen carbonate solution and common salt solution, dried over magnesium sulphate and concentrated in vacuo.

13.6 g (94% of theory) of 5-amino-4-dichlorofluoromethanesulphenyl-1-(2,6-dichloro-4-trifluoromethyl-phenyl)pyrazole of melting point 100° C.–103° C. are obtained.

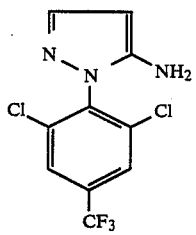

24.5 g (0.1 mole) of 2,6-dichloro-4-trifluoromethyl-phenylhydrazine and 20 mg of disodium ethylene-diamine-tetraacetate (=Titriplex III) in 150 ml of methanol are treated dropwise with 25 ml (27.6 g/0.3 mole) of 2-chloroacrylonitrile at the reflux temperature. When the addition is complete, the mixture is heated for a further 8 hours at the reflux temperature, 9 ml (0.16 mole) of 96% strength sulphuric acid are added dropwise, and the mixture is heated for a further 6 hours at the reflux temperature. The cooled reaction mixture is treated with 33.5 g (0.3 mole) of anhydrous sodium carbonate. After 4 hours, the solvent is removed in vacuo. The residue is taken up in 500 ml of water and stirred for 10 hours at room temperature. The precipitate which deposits is filtered off, rinsed with water and dried in vacuo at 50° C.

28.5 g (96% of theory) of 5-amino-1-(2,6-dichloro-4-trifluoromethylphenyl)-pyrazole of melting point 103° C.–105° C. are obtained.

Example 2

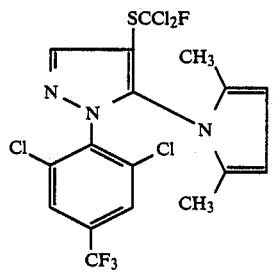

5 g (0.013 mole) of 5-amino-4-dichlorofluoromethylthio-1-(2,6-dichloro-4-trifluoromethyl-phenyl)-pyrazole and 3 g (0.026 mole) of acetonyl acetone, together with 0.5 g of p-toluenesulphonic acid, are refluxed for 24 hours in 150 ml of toluene over a water separator. For work-up, the solvent is removed in vacuo. 6.0 g (94% of theory) of 1-(2,6-dichloro-4-trifluoromethyl-phenyl)-5-(2,5-dimethyl-pyrrol-1-yl)-4-dichlorofluoromethylsulphenyl-pyrazole of melting point 72° C.–75° C. are obtained.

Example 3

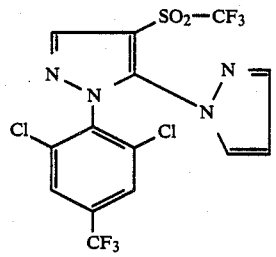

1.2 ml (0.0078 mole) of 1,1,3,3-tetramethoxypropane and 0.2 ml (0.0034 mole) of 96 percent strength sulphuric acid are added in sequence to 3 g (0.0068 mole) of 5-hydrazino-4-(trifluoromethylsulphonyl)-1-(2,6-dichloro-4-trifluoromethyl-phenyl)-pyrazole in 7 ml of ethanol at 20° C. to 25° C. The reaction mixture is heated at the reflux temperature for 2 hours, cooled, and neutralized with 0.36 g (0.0034 mole) of sodium carbonate, and the solvent is removed in vacuo. The residue is suspended in water, filtered, washed again with water and dried. 2.5 g (77% of theory) of 1-(2,6-dichloro-4-trifluoromethyl-phenyl)-5-(pyrazol-1-yl)-4-trifluoromethylsulphonyl-pyrazole of melting point 127° C. to 133° C. are obtained.

In a corresponding fashion and according to the general information for the preparation, the following 5-heterocyclyl-1-aryl-pyrazoles of the general formula (I) are obtained:

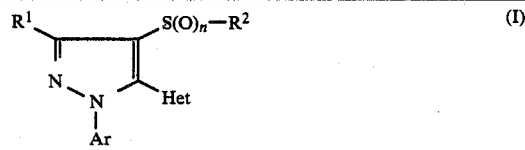

| Example No. | $R^1$ | $-S(O)_n-R^2$ | Het | Ar | Melting point/°C. |
|---|---|---|---|---|---|
| 4 | H | $-SCCl_2F$ | 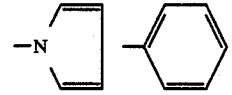 | | 118–122° C. |
| 5 | H | $-SCF_3$ | 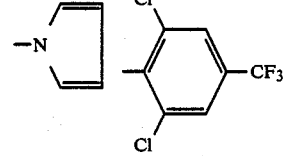 | | 59–63° C. |

-continued

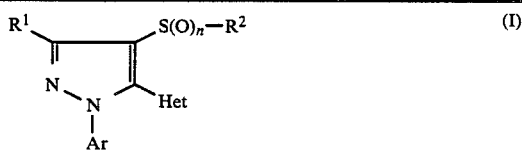

| Example No. | R¹ | —S(O)ₙ—R² | Het | Ar | Melting point/°C. |
|---|---|---|---|---|---|
| 6 | H | —SCCl₂F | —N (pyrrolyl) | 2,4,6-trichlorophenyl | 97–100° C. |
| 7 | H | —SCCl₂F | —N (pyrrolyl) | 2,6-dichloro-4-(SO₂CF₃)phenyl | 90–96° C. |
| 8 | H | —SO₂—CCl₂F | —N (pyrrolyl) | 2,6-dichloro-4-CF₃-phenyl | 122° C. |
| 9 | H | —SCF₃ | —N (pyrrolyl) | 2-chloro-4-OCF₃-phenyl | boiling point 150° C./ 0.4 mbar |
| 10 | H | —SCCl₂F | —N (pyrrolyl) | 2-chloro-4-CF₃-phenyl | ¹H—NMR*: 6.24; 6.66 |
| 11 | H | —SCF₃ | —N (pyrrolyl) | 2,4,6-trichlorophenyl | ¹H—NMR*: 6.19; 6.69 |
| 12 | H | —SCCl₂F | —N (pyrrolyl) | 2-Cl-4-CF₃-6-Br-phenyl | 102–104° C. |
| 13 | H | —SCCl₂F | —N (pyrrolyl) | 2-Br-4-Br-6-Cl-phenyl | 117–121° C. |

-continued $$\underset{Ar}{\underset{|}{N}}\underset{\parallel}{\overset{R^1\quad S(O)_n-R^2}{\diagdown\diagup}}\text{Het} \quad (I)$$

| Example No. | R[1] | —S(O)ₙ—R² | Het | Ar | Melting point/°C. |
|---|---|---|---|---|---|
| 14 | H | —SCCl₂F | pyrrol-1-yl | 2,6-dichloro-4-bromophenyl | 113–118° C. |
| 15 | H | —S(O)—CCl₂F | pyrrol-1-yl | 2-chloro-6-bromo-4-trifluoromethylphenyl | 111–118° C. |
| 16 | H | —SO₂—CCl₂F | pyrazol-1-yl | 2,6-dichloro-4-trifluoromethylphenyl | 145–150° C. |
| 17 | H | —S—CClF₂ | pyrrol-1-yl | 2-chloro-6-bromo-4-trifluoromethylphenyl | 93–98° C. |
| 18 | H | —S(O)—CF₃ | pyrrol-1-yl | 2,6-dichloro-4-trifluoromethylphenyl | 75–79° C. |
| 19 | H | —SO₂—CF₃ | pyrrol-1-yl | 2,6-dichloro-4-trifluoromethylphenyl | 62–66° C. |
| 20 | CH₃ | —SCCl₂F | pyrrol-1-yl | 2,6-dichloro-4-trifluoromethylphenyl | ¹H—NMR*: 6.23; 6.74 |
| 21 | CH₃ | —SCF₃ | pyrrol-1-yl | 2,6-dichloro-4-trifluoromethylphenyl | ¹H—NMR*: 6.22; 6.72 |

-continued
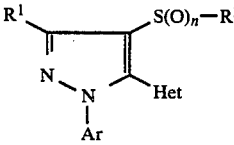
| Example No. | R¹ | —S(O)ₙ—R² | Het | Ar | Melting point/°C. |
|---|---|---|---|---|---|
| 22 | H | —SCH₃ |  | 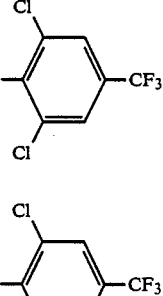 | 54–56° C. |
| 23 | H | —SC₂H₅ | 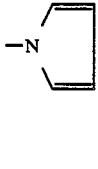 | 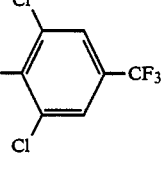 | 81° C. |
| 24 | H | —SO₂—C₂H₅ | 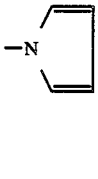 | 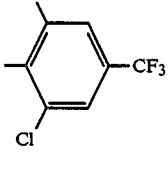 | 110° C. |
| 25 | CH₃ | —S—C₂H₅ |  | 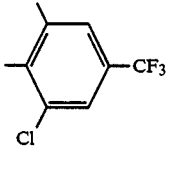 | 62° C. |
| 26 | CH₃ | —S—CF₃ |  | 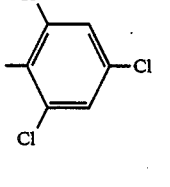 | ¹H—NMR*: 6.24; 6.76 |
| 27 | CH₃ | —S—CCl₂F |  | 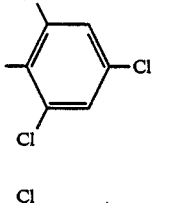 | ¹H—NMR*: 6.16; 6.70 |
| 28 | CH₃ | —S—CClF₂ |  | 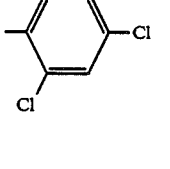 | ¹H—NMR*: 6.17; 6.67 |

-continued
$$\text{(I)}$$
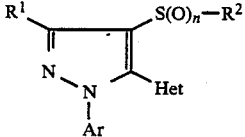
| Example No. | $R^1$ | $-S(O)_n-R^2$ | Het | Ar | Melting point/°C. |
|---|---|---|---|---|---|
| 29 | $CH_3$ | $-SCF_3$ |  | 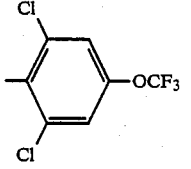 | $^1H$—NMR*: 6.17; 6.70 |
| 30 | $CH_3$ | $-S-CCl_2F$ |  | 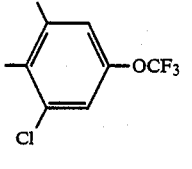 | $^1H$—NMR*: 6.18; 6.71 |
| 31 | $CH_3$ | $-S-CClF_2$ |  | 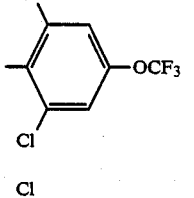 | $^1H$—NMR*: 6.18; 6.70 |
| 32 | H | $-S-CClF_2$ |  | 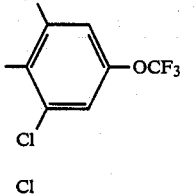 | boiling point 200° C./ 0.01 mbar |
| 33 | $CH_3$ | $-S-CClF_2$ |  | 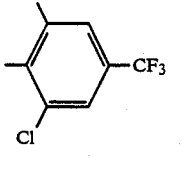 | $^1H$—NMR*: 6.17; 6.67 |
| 34 | H | $-SO_2-CClF_2$ |  | 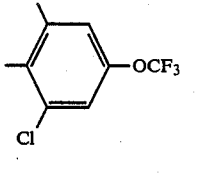 | boiling point 165° C. 0.01 mbar |
| 35 | $CH_3$ | $-S-CCl_2F$ |  | 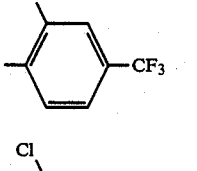 | Oil |
| 36 | $CH_3$ | $-S-CClF_2$ |  | 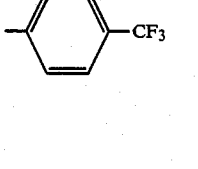 | Oil |

-continued

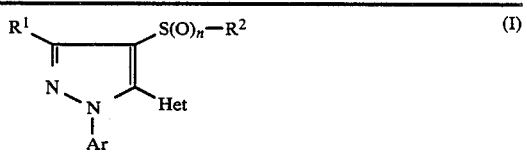

| Example No. | R¹ | —S(O)$_n$—R² | Het | Ar | Melting point/°C. |
|---|---|---|---|---|---|
| 37 | $CH_3$ | —S—$CF_3$ | —N (pyrrolyl) | 2,4-Cl, $CF_3$-phenyl | Oil |
| 38 | $CH_3$ | —S(O)—$CF_3$ | —N (pyrrolyl) | 2,6-Cl$_2$-4-$CF_3$-phenyl | 96–97° C. |
| 39 | $CH_3$ | —$SO_2$—$CF_3$ | —N (pyrrolyl) | 2,6-Cl$_2$-4-$CF_3$-phenyl | Oil |
| 40 | H | —S(O)—$CCl_2F$ | —N (pyrrolyl) | 2,6-Cl$_2$-4-$CF_3$-phenyl | 123–124° C. |
| 41 | H | —S—$CClF_2$ | —N (pyrrolyl) | 2,6-Cl$_2$-4-$CF_3$-phenyl | 97–98° C. |
| 42 | H | —S—$CClF_2$ | —N (pyrrolyl) | 2,6-Br$_2$-4-$CF_3$-phenyl | 106–109° C. |
| 43 | H | —S—$CF_3$ | 2,5-di-$CH_3$-pyrrolyl | 2,6-Cl$_2$-4-$CF_3$-phenyl | Oil |

*The ¹H—NMR spectra were recorded in CDCl$_3$ with tetramethylsilane (TMS) as internal standard. δ values are given in ppm.

PREPARATION OF THE STARTING COMPOUNDS OF THE FORMULA IV

Example IV-1

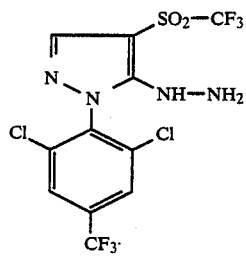

2.5 ml (0.065 mole) of hydrazine hydrate are added to 10 g (0.02 mole) of 5-bromo-1-(2,6-dichloro-4-trifluoromethyl-phenyl)-4-trifluoromethylsulphonyl-pyrazole in 140 ml of dioxane at room temperature and the mixture is warmed at 60° C. with stirring for 4 hours. For work-up, the solvent is removed in vacuo and the oil remaining is purified by chromatography (silica gel, eluent: dichloromethane). 6.5 g (72% of theory) of 1-(2,6-dichloro-4-trifluoromethyl-phenyl)-5-hydrazino-4-trifluoromethylsulphonyl-pyrazole of melting point 154° C. are obtained.

PREPARATION OF THE STARTING COMPOUND

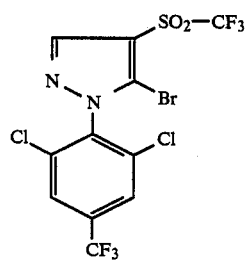

A suspension of 28 g (0.065 mole) of 5-amino-1-(2,6-dichloro-4-trifluoromethyl-phenyl)-4-trifluoromethyl-sulphonyl-pyrazole in 70 ml of bromoform are added to a solution of 15.5 ml (0.13 mole) of t-butyl nitrite in 30 ml of bromoform at 20° C. to 25° C. The temperature rises to 40° C. The mixture is then stirred for 15 hours at room temperature, 200 ml of dichloromethane are added, the mixture is washed in sequence with aqueous sodium hydrogen carbonate, sodium thiosulphate and sodium chloride solution, the organic phase is dried over magnesium sulphate and the solvent is removed in vacuo. The oil remaining is purified by chromatography (silica gel, eluent: dichloromethane). 13.8 g (43% of theory) of 5-bromo-1-(2,6-dichloro-4-trifluoromethyl-phenyl)-4-trifluoromethylsulphonylpyrazole of melting point 90° C. to 91° C. are obtained.

In corresponding fashion and according to the general information for the preparation, the following 5-hydrazino-1-aryl-pyrazoles of the general formula (IV) are obtained:

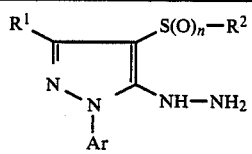

| Example No. | $R^1$ | $-S(O)_n-R^2$ | Ar | Melting point/°C. |
|---|---|---|---|---|
| IV-2 | H | $-SO_2-CCl_2F$ | 2,6-dichloro-4-CF$_3$-phenyl | 172–173° C. |
| IV-3 | H | $-SO_2-CCl_2F$ | 2-chloro-4-Br-phenyl (2,4-Cl-Br) | 153–168° C. |
| IV-4 | H | $-SCCl_2F$ | 2,6-dichloro-4-CF$_3$-phenyl | |

USE EXAMPLES

In the use examples which follow, the compounds listed below were employed as comparison substance:

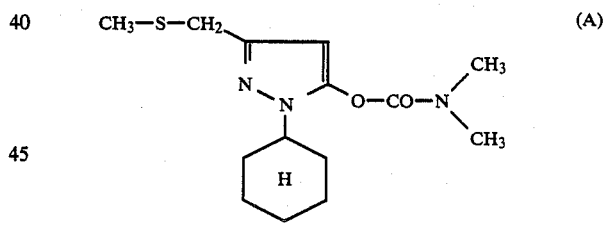

1-Cyclohexyl-5-[N,N-(dimethyl)-carbamoyloxy]-3-methyl-thiomethyl-pyrazole (known from DE-OS (German Published Specification) No. 2,839,270);

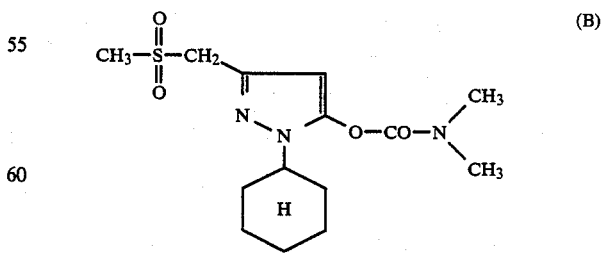

1-Cyclohexyl-5-[N,N-(dimethyl)-carbamoyloxy]-3-methyl-sulphonylmethyl-pyrazole (known from DE-OS (German Published Specification) No. 2,839,270).

Example A

Phaedon larvae test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the specified period of time, the destruction in % is determined. 100% means that all the beetle larvae have been killed; 0% means that none of the beetle larvae have been killed.

In this test, the following compounds of the preparation examples, for example, demonstrate superior effectiveness compared to the state of the art: 1, 2, 5, 8, 10, 12, 15, 16, 17, 18, 19 and 34.

Example B

Plutella test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) were treated by being dipped into the preparation of active compound of the desired concentration and are infested with caterpillars of the diamond-back moth (*Plutella maculipennis*), as long as the leaves are still moist.

After the specified periods of time, the destruction in % is determined. 100% means that all the caterpillars have been killed; 0% means that none of the caterpillars have been killed.

In this test, the following compounds of the preparation examples, for example, demonstrate superior effectiveness compared to the state of the art: 1, 2, 5, 8, 10, 12, 15, 16, 17, 18, 19 and 34.

Example C

Test insect: *Phorbia antiqua* maggots (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount of weight of active compound per unit volume of soil, which is given in ppm (=mg/l), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, the following compounds of the preparation examples, for example, demonstrate superior effectiveness compared to the state of the art: 1, 5, 10, 12, 19, IV-2.

Example D

Root-systemic Action

Test insect: *Phaedon cochleariae* larvae
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test insect after 7 days. After a further 2 days, the evaluation is made by counting or estimating the dead insects. The root-systemic action of the active compound is deduced from the mortality figures. It is 100% if all test insects have been killed and 0% if just as many test insects are still alive as in the case of the untreated control.

In this test, the following compound of the preparation example, for example, demonstrates superior action compared to the state of the art: 5.

Example E

Test insect: *Musca domestica* grubs (resistant)
Number of test insects: 25
Solvent: Acetone 2 parts by weight of active compound are taken up in 1,000 parts by volume of solvent. The solution thus obtained is diluted with further solvent to the desired lower concentrations.

2.5 ml of the active compound solution are pipetted into a Petri dish. A filterpaper disc of about 9.5 cm diameter is located on the bottom of the Petri dish. The Petri dish is left standing open until the solvent has completely evaporated. The amount of active compound per $m^2$ of filterpaper varies, depending on the concentration of the active compound solution. The stated number of test insects is then introduced into the Petri dish, and the dish is covered with a glass lid.

14 days after start-up of the test, the number of flies hatching from the maggots is evaluated according to Abbott and the prevention from hatching is expressed in %.

In this test, the following compounds of the preparation examples, for example, demonstrate superior action compared to the state of the art: 1, 2, 3, 5, 8, 9, 10, 11, 12, 16, 17, 18, 19, 20, 21, 22 and 23, as well as IV-2 and IV-4.

Example F

Test insects: *Sitophilus granarius*
Number of test insects: 25
Solvent: Acetone 2 parts by weight of active compound are taken up in 1,000 parts by volume of solvent. The solution thus obtained is diluted with further solvent to the desired concentrations.

2.5 ml of the active compound solution are pipetted into a Petri dish. A filterpaper disc of about 9.5 cm diameter is located on the bottom of the Petri dish. The Petri dish is left standing open until the solvent has completely evaporated. The amount of active compound per m² of filterpaper varies, depending on the concentration of the active compound solution. The stated number of test insects is then introduced into the Petri dish, and the dish is covered with a glass lid.

The condition of the test insects is checked 3 days after the experiments have been set up. The destruction in % is determined. 100% means that all the test insects have been killed; 0% means that none of the test insects have been killed.

In this test, the following compounds of the preparation examples, for example, demonstrate superior action compared to the state of the art: 1, 2, 3, 5, 9, 10, 11, 12, 14, 16, 17, 18, 19, 20, 21, 22, 23, 26, 27, 28, 29, 30, 31, 32, 33, 34, IV-1 and IV-2.

Example G

Test with *Lucilia cuprina* larvae (OP res. Goondiwindi strain)
Emulsifier:
  35 parts by weight of ethylene glycol monomethyl ether
  35 parts by weight of nonylphenol polyglycol ether To produce a suitable preparation of active compound, three parts by weight of active compound are mixed with seven parts by weight of the abovementioned solvent mixture and the concentrate thus obtained is diluted with water to the particular desired concentration.

About 20 *Lucilia cuprina* res. larvae are introduced into a test tube which contains approx. 1 cm² of horse muscle and 0.5 ml of the preparation of active compound. After 24 hours, the degree of destruction is determined.

In this test, the following compounds of the preparation examples, for example, demonstrate superior action compared to the state of the art: 1 and 2.

It is understood that the specification and examples are illustrative but not limitative of the present invention and that other embodiments within the spirit and scope of the invention will suggest themselves to those skilled in the art.

We claim:

1. A 5-heterocyclyl-1-aryl-pyrazole of the formula

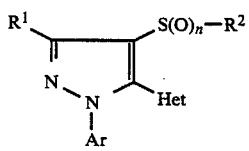

in which $R^1$ represents in each case straight-chain or branched alkyl or haloalkyl having 1 to 4 carbon atoms and, if appropriate, 1 to 9 identical or different haloatoms or represents hydrogen, $R^2$ represents in each case straight-chain or branched alkyl, alkenyl or alkinyl having in each case up to 8 carbon atoms, represents in each case straight-chain or branched haloalkyl or haloalkenyl having in each case up to 8 carbon atoms and up to 17 identical or different haloatoms, represents cycloalkyl having 3 to 7 carbon atoms or represents in each case optionally singly or multiply, identically or differently substituted phenylalkyl or phenyl having, if appropriate, 1 to 4 carbon atoms in the straight-chain or branched alkyl part, phenyl substituents in each case being halogen, cyano, nitro, in each case straight-chain or branched alkyl, alkoxy, alkylthio, alkylsulphinyl, alkylsulphonyl, haloalkyl, haloalkoxy, haloalkylsulphinyl or haloalkylsulphonyl having in each case 1 to 4 carbon atoms in the individual alkyl parts and, if appropriate, 1 to 9 identical or different haloatoms, Ar represents in each case optionally singly or multiply, identically or differently substituted phenyl, 2-pyridyl, 3-pyridyl or 4-pyridyl, substituents being cyano, nitro, halogen, in each case straight-chain or branched alkyl, alkoxy or alkoxycarbonyl having in each case up to 4 carbon atoms, in addition in each case straight-chain or branched haloalkyl or haloalkoxy having in each case up to 4 carbon atoms and up to 9 identical or different haloatoms or an $S(O)_m$—$R^7$ radical, $R^7$ represents amino, or in each case straight-chain or branched alkyl, alkylamino, dialkylamino or haloalkyl having in each case up to 4 carbon atoms in the individual alkyl parts and, in the case of the haloalkyl, having up to 9 identical or different haloatoms, m and n each independently represents a number 0, 1 or 2, and Het represents

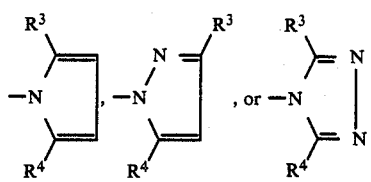

where $R^3$ and $R^4$, independently of one another, represent in each case hydrogen, straight-chain or branched alkyl having 1 to 4 carbon atoms, or phenyl.

2. A 5-heterocyclyl-1-aryl-pyrazole according to claim 1, in which $R^1$ represents hydrogen, methyl, ethyl, n- or i-propyl or trifluoromethyl, $R^2$ represents methyl, ethyl, n- or i-propyl, n-, i-, s- or t-butyl, n- or i-pentyl, n- or i-hexyl, allyl, propenyl, butenyl, propargyl, butinyl, cyclopropyl, cyclopentyl, cyclohexyl, chloromethyl, difluoromethyl, difluorochloromethyl, fluorodichloromethyl, trifluoromethyl, pentafluoroethyl, pentachloroethyl, fluorotetrachloroethyl, difluorotetrachloroethyl, trifluorodichloroethyl, tetrafluorochloroethyl, heptafluoropropyl, chloroethyl, bromoethyl, chloropropyl, chloropropenyl, dichloropropenyl, chlorobutenyl, or in each case optionally singly to triply, identically or differently substituted phenyl, benzyl or phenylethyl, phenyl substituents being fluorine, chlorine, bromine, iodine, cyano, nitro, methyl, ethyl, methoxy, methylthio, trifluoromethyl, methylsulphinyl, methylsulphonyl, trifluoromethoxy, trifluoromethylthio, trifluoromethylsulphinyl or trifluoromethylsulphonyl, Ar represents in each case optionally singly to quintuply, indentically or differently substituted phenyl, 2-pyridyl, 3-pyridyl or 4-pyridyl, suitable substituents being cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, difluorochloromethyl, difluorochloromethyl, chloromethyl, dichloromethyl, difluoromethyl, pentafluoroethyl, tetrafluoroethyl, trifluorochloroethyl, trifluoroethyl, difluorodichloromethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an —S(O)$_m$R$^7$ radical where R$^7$ represents amino, methylamino, ethylamino, dimethylamino, diethylamino, fluorodichloromethyl, difluoromethyl, tetrafluoroethyl, trifluorochloroethyl, trifluoromethyl, methyl or ethyl, m represents a number 0, 1 or 2, and Het represents a heterocycle of the formula

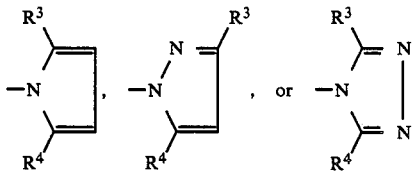

where

R$^3$ and R$^4$, independently of one another, in each case represent hydrogen, methyl, ethyl, n- or i-propyl or phenyl.

3. A compound according to claim 1, wherein such compound is 1-(2,6-dichloro-4-trifluoromethyl-phenyl)-5-(pyrrol-1-yl)-4-dichlorofluoromethylsulphenyl-pyrazole of the formula

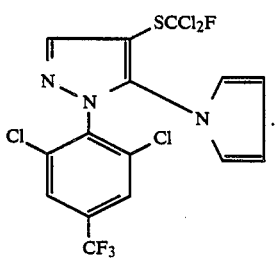

4. A compound according to claim 1, wherein such compound is 1-(2,6-dichloro-4-trifluoromethyl-phenyl)-5-(pyrrol-1-yl)-4-trifluoromethylsulphenyl-pyrazole of the formula

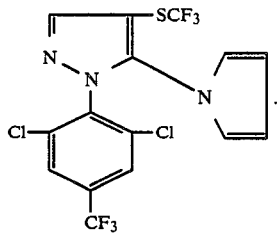

5. A compound according to claim 1, wherein such compound is 1-(2,6-dichloro-4-trifluoromethyl-phenyl)-5-(pyrrol-1-yl)-4-dichlorofluoromethylsulphonyl-pyrazole of the formula

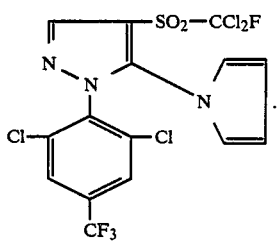

6. A compound according to claim 1, wherein such compound is 1-(2-chloro-4-trifluoromethoxy-phenyl)-5-pyrrol-1-yl)-4-trifluoromethylsulphenyl-pyrazole of the formula

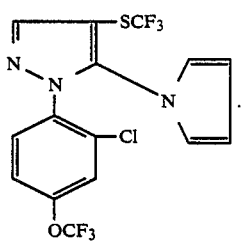

7. A compound according to claim 1, wherein such compound is 1-(2-chloro-4-trifluoromethyl-phenyl)-5-(pyrrol-1-yl)-4-trifluoromethylsulphenyl-pyrazole of the formula

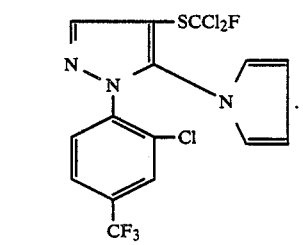

8. A compound according to claim 1, wherein such compound is 1-(2-bromo-6-chloro-4-trifluoromethyl-phenyl)-5-(pyrrol-1-yl)-4-dichlorofluoromethylsulphenyl-pyrazole of the formula

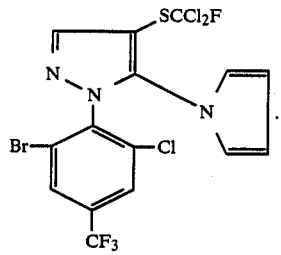

9. A compound according to claim 1, wherein such compound is 1-(2-bromo-6-chloro-4-trifluoromethyl-phenyl)-5-(pyrrol-1-yl)-4-dichlorofluoromethylsulphinyl-pyrazole of the formula

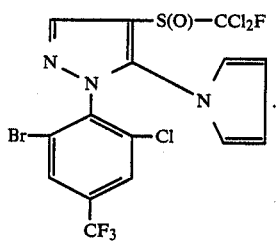

10. A compound according to claim 1, wherein such compound is 1-(2,6-dichloro-4-trifluoromethyl-phenyl)-5-(pyrrol-1-yl)-4-trifluoromethylsulphinyl-pyrazole of the formula

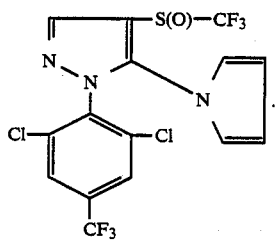

11. A compound according to claim 1, wherein such compound is 1-(2,6-dichloro-4-trifluoromethyl-phenyl)-5-(pyrrol-1-yl)-4-trifluoromethylsulphonyl-pyrazole of the formula

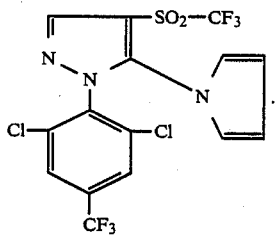

12. An insecticidal, arachnicidal or nematocidal composition comprising an insecticidally, arachnicidally or nematocidally effective amount of a compound according to claim 1 in admixture with a diluent.

13. A method of combating insects, arachnids or nematodes which comprises applying thereto or to a habitat thereof an insecticidally, arachnicidally or nematocidally effective amount of a compound according to claim 1 in admixture with a diluent.

14. The method according to claim 13, wherein such compound is
1-(2,6-dichloro-4-trifluoromethyl-phenyl)-5-(pyrrol-1-yl)-4-dichlorofluoromethylsulphenylpyrazole,
1-(2,6-dichloro-4-trifluoromethyl-phenyl)-5-(pyrrol-1-yl)-4-trifluoromethylsulphenyl-pyrazole,
1-(2,6-dichloro-4-trifluoromethyl-phenyl)-5-(pyrrol-1-yl)-4-dichlorofluoromethylsulphonylpyrazole,
1-(2-chloro-4-trifluoromethoxy-phenyl)-5-(pyrrol-1-yl)-4-trifluoromethylsulphenylpyrazole,
1-(2-chloro-4-trifluoromethyl-phenyl)-5-(pyrrol-1-yl)-4-trifluoromethylsulphenyl-pyrazole,
1-(2-bromo-6-chloro-4-trifluoromethyl-phenyl)-5-(pyrrol-1-yl)-4-dichlorofluoromethylsulphenylpyrazole,
1-(2-bromo-6-chloro-4-trifluoromethyl-phenyl)-5-(pyrrol-1-yl)-4-dichlorofluoromethylsulphinylpyrazole,
1-(2,6-dichloro-4-trifluoromethyl-phenyl)-5-(pyrrol-1-yl)-4-trifluoromethylsulphinyl-pyrazole or
1-(2,6-dichloro-4-trifluoromethyl-phenyl)-5-(pyrrol-1-yl)-4-trifluoromethylsulphonylpyrazole.

15. A 5-hydrazino-1-aryl-pyrazole of the formula

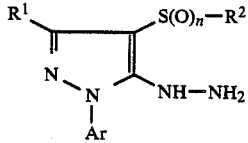

in which
$R^1$ represents in each case straight-chain or branched alkyl or haloalkyl having 1 to 4 carbon atoms and, if appropriate, 1 to 9 identical or different haloatoms or represents hydrogen,
$R^2$ represents in each case straight-chain or branched alkyl, alkenyl or alkinyl having in each case up to 8 carbon atoms, represents in each case straight-chain or branched haloalkyl or haloalkenyl having in each case up to 8 carbon atoms and up to 17 identical or different haloatoms, represents cycloalkyl having 3 to 7 carbon atoms or represents in each case optionally singly or multiply, identically or differently substituted phenylalkyl or phenyl having, if appropriate, 1 to 4 carbon atoms in the straight-chain or branched alkyl part, phenyl substituents in each case being halogen, cyano, nitro, in each case straight-chain or branched alkyl, alkoxy, alkylthio, alkylsulphinyl, alkylsulphonyl, haloalkyl, haloalkoxy, haloalkylsulphinyl or haloalkylsulphonyl having in each case 1 to 4 carbon atoms in the individual alkyl parts and, if appropriate, 1 to 9 identical or different haloatoms,
Ar represents in each case optionally singly or multiply, identically or differently substituted phenyl, 2-pyridyl, 3-pyridyl or 4-pyridyl, substituents being cyano, nitro, halogen, in each case straight-chain or branched alkyl, alkoxy or alkoxycarbonyl having in each case up to 4 carbon atoms, in addition in each case straight-chain or branched haloalkyl or haloalkoxy having in each case up to 4 carbon atoms and up to 9 identical or different haloatoms or an $S(O)_m$—$R^7$ radical,
$R^7$ represents amino, methylamino, ethylamino, dimethylamino, diethylamino, fluorodichloromethyl, difluoromethyl, tetrafluoroethyl, trifluorochloroethyl, trifluoromethyl, methyl or ethyl,
m represents a number 0, 1 or 2, and
n represents a number 9, 1 or 2.

16. A bis-(pyrazolyl)disulphide of the formula

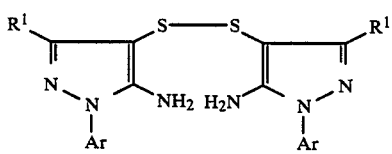

in which

R[1] represents in each case straight-chain or branched alkyl or haloalkyl having 1 to 4 carbon atoms and, if appropriate, 1 to 9 identical or different haloatoms or represents hydrogen, Ar represents in each case optionally singly or multiply, identically or differently substituted phenyl, 2-pyridyl, 3-pyridyl or 4-pyridyl, substituents being cyano, nitro, halogen, in each case straight-chain or branched alkyl, alkoxy or alkoxycarbonyl having in each case up to 4 carbon atoms, in addition in each case straight-chain or branched haloalkyl or haloalkoxy having in each case up to 4 carbon atoms and up to 9 identical or different haloatoms or an $S(O)_m$—$R^7$ radical, $R^7$ represents amino, methylamino, ethylamino, dimethylamino, diethylamino, fluorodichloromethyl, difluoromethyl, tetrafluoroethyl, trifluorochloroethyl, trifluoromethyl, methyl or ethyl, m represents a number 0, 1 or 2, and n represents a number 0, 1 or 2.

17. An insecticidal, arachnididal or nematocidal composition comprising an insecticidally, arachnicidally or nematocidally effective amount of a compound according to claim 15 in admixture with a diluent.

18. A method of combating insects, arachnids or nematodes which comprises applying thereto or to a habitat thereof an insecticidally, arachnicidally or nematocidally effective amount of a compound according to claim 15 in admixture with a diluent.

* * * * *

UNITED STATES PATENT AND TRADEMARK OFFICE
CERTIFICATE OF CORRECTION

PATENT NO. : 4,803,215
DATED : February 7, 1989
INVENTOR(S) : Uta Jensen-Korte, et al It is certified that error appears in the above-identified patent and that said Letters Patent is hereby corrected as shown below:

| | |
|---|---|
| Col. 18, line 33 | After "such" delete "s" and substitute --as-- |
| Col. 20, line 15 | Bottom of formula delete " \| " and substitute $--\underset{CF_3}{\overset{Cl}{|}}--$ |
| Col. 35, line 63 | Before "weight" delete "of" and substitute --by-- |
| Col. 38, line 3 | Correct --haloatoms-- |

Signed and Sealed this

Ninth Day of January, 1990

Attest:

JEFFREY M. SAMUELS

Attesting Officer     Acting Commissioner of Patents and Trademarks